United States Patent

Mandal

[11] Patent Number: 6,114,584
[45] Date of Patent: Sep. 5, 2000

[54] METHOD OF PREPARING BROMINATED SUBSTITUTED ANILINES

[75] Inventor: Sanjay Mandal, Grand Island, N.Y.

[73] Assignee: Occidental Chemical Corporation, Dallas, Tex.

[21] Appl. No.: 09/408,403

[22] Filed: Sep. 29, 1999

[51] Int. Cl.⁷ .................................................. C07C 209/00
[52] U.S. Cl. .......................................... 564/412; 564/442
[58] Field of Search ..................................... 564/412, 442

[56] References Cited

U.S. PATENT DOCUMENTS

| | | | |
|---|---|---|---|
| 4,404,402 | 9/1983 | Ladmer et al. .......................... | 564/442 |
| 5,045,554 | 9/1991 | Alt et al. ................................. | 514/365 |

OTHER PUBLICATIONS

G. H. Coleman et al., Organic Synthesis, Wiley, New York (1943), collected vol. II, pp. 592 to 594. Month Unavailable.
Giorgio Cerichell et al., "Surfactant Control of the Ortho/Para Ratio in the Bromination of Anilines," *Tetrahedron Letters*, vol. 30, No. 45, pp. 6209–6210 (1989); Month Unavailable.

*Primary Examiner*—Samuel Barts
*Attorney, Agent, or Firm*—Anne E. Brooks; Richard D. Fuerle

[57] ABSTRACT

Disclosed is a method of preparing brominated substituted anilines. A mixture in water is formed of a substituted aniline having the general formula

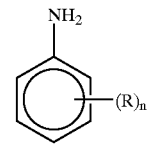

where each R is independently selected from halogen, alkyl and haloalkyl from $C_1$ to $C_{12}$, aryl, alkaryl, and aralkyl from $C_6$ to $C_{12}$, R does not occupy all three 2, 4, and 6 positions, and n is 1 to 4. To the suspension is added about 1.0 to about 1.1 equivalents of bromine for each bromine atom to be substituted onto the aromatic ring of said substituted aniline. No acid is present during the reaction.

20 Claims, No Drawings

METHOD OF PREPARING BROMINATED SUBSTITUTED ANILINES

BACKGROUND OF THE INVENTION

This invention relates to a method of brominating substituted anilines. In particular, it relates to a method in which a substituted aniline is brominated in water in the absence of any acid.

4-Trifluoromethoxy-2,6-dibromoaniline (TFMDBA) is used to make herbicides and other chemicals. It can be made by reacting 4-aminotrifluoromethoxy benzene (TFMB) with bromine in a solution of 10 times acetic acid and 2 equivalents of sodium acetate. (See U.S. Pat. No. 5,045,554, column 5, line 62, to column 6, line 3.) The large amount of acetic acid that that reaction requires is expensive for an industrial process.

It is also known that 2,4,6-tribromo aniline can be made by reacting aniline with bromine in 50 times water containing about 1 equivalent of hydrochloric acid. (See *Organic Synthesis*, Wiley; New York, 1943; collected vol. II, pages 592 to 594.) The hydrochloric acid is used to prevent the formation of the bromide salt, which would remain in solution, while 2,4,6-tribromo aniline is insoluble in water and precipitates.

SUMMARY OF THE INVENTION

We have discovered that TFMDBA and other brominated substituted anilines can be made by brominating the corresponding substituted aniline in water without any acid being present. Contrary to the expectations of the prior art, the bromide salt does not form and the desired product precipitates and can be easily isolated. In our process it is not necessary to dispose of any acids or organic solvents and yields of over 90% have been obtained.

DESCRIPTION OF THE PREFERRED EMBODIMENTS

The method of this invention is applicable to substituted anilines having the general formula:

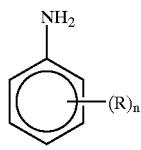

where each R is independently selected from halogen, alkyl and haloalkyl from $C_1$ to $C_{12}$, aryl, alkaryl, and aralkyl from $C_6$ to $C_{12}$, and n is 1 to 4. The R group or groups can be in any position on the ring but cannot occupy all three of the 2, 4, and 6 positions (with respect to the amino group) as at least one of those positions must be available for bromination (bromination occurs only at those positions). None of the R groups are acidic and there are no other acidic groups on the substituted aniline. The preferred R groups are trifluoromethoxy, and trifluoromethyl as they are economically more important; the most preferred R group is trifluoromethoxy. Preferably, n is 1 with the single R group is in the para position because this produces dibromo anilines, which are more important commercially.

The bromination is performed in water in the absence of any acid. That is, no inorganic acid, no carboxylic acid, no sulphonic acid, and no Lewis acid is present during the reaction. The substituted aniline is an insoluble solid or a water-immiscible liquid. If it is a solid, it forms a suspension with water and if it is a liquid, two phases are formed. Sufficient water should be used to form a stirable mixture and excess water should be avoided as it confers no additional benefit and merely increases the throughput; about 2 to about 3 pbw (parts by weight) of water is preferred for each pbw of substituted aniline to be brominated.

About 1.0 to about 1.1 equivalents of liquid bromine should be used per equivalent of the substituted aniline for each bromine atom that is to be substituted onto the aniline aromatic ring as less will leave unreacted substituted aniline and more is unnecessary. One to three bromine atoms can be substituted onto the ring.

The reaction is exothermic and can be performed at a temperature of about room temperature to about 60° C.; lower temperatures are slower and higher temperatures may result in the loss of bromine and the production of colored byproducts. It is preferable to heat the solution of the substituted aniline in water to about 40 to about 50° C., then add the bromine, and maintain the reaction within that range until it is complete. The mixture should be stirred vigorously to minimize the production of byproducts. The product of the bromination is the brominated substituted aniline, not a bromide salt; no intermediate bromide salt is formed in the process of this invention.

For each bromine that goes onto the aromatic ring of the substituted aniline, one equivalent of hydrogen bromide is formed. In a preferred embodiment of the method of this invention, the product is separated from the reaction mixture by filtration and an oxidizing agent is added to the filtrate to oxidize this hydrogen bromide byproduct to elemental bromine. The elemental bromine is vaporized (bp=58.77° C.), collected, and recycled. Examples of oxidizing agents that can be used include chlorine gas and sodium chlorate. The preferred oxidizing agent is chlorine gas as it is very effective. About 1 to about 1.2 equivalents of oxidizing agent should be used for each equivalent of hydrogen bromide that is present as less will leave unoxidized hydrogen bromide and more is unnecessary.

The brominated substituted aniline product is a water-insoluble solid and precipitates. It can be collected by filtering or another method and washed with water.

The following examples further illustrated this invention:

EXAMPLE 1

A mixture of 177 g of TFMB (1 mole) and 531 g of water were placed in a 1 L jacketed glass reactor equipped with a watercooled condenser, a thermocouple, a mechanical stirrer, and an inlet for liquid bromine. The reactor was heated to 35 to 40° C. Over a period of 2 hours, 320 g of liquid bromine (2 mole) was added with vigorous stirring. The temperature of the reactor was maintained at 50° C. Solid product was precipitating out as the bromine addition continued. After cooling the reactor to room temperature, the slurry of the product in water was filtered and washed with water followed by vacuum drying. The yield of the product was >95%. The crude off-white product obtained in this reaction was >99.0% pure.

What is claimed is:

1. A method of making a brominated substituted aniline comprising (A) forming a mixture in water of a substituted aniline having the general formula

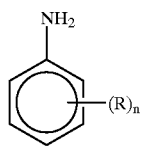

where each R is independently selected from halogen, alkyl and haloalkyl from $C_1$ to $C_{12}$, aryl, alkaryl, and aralkyl from $C_6$ to $C_{12}$, R does not occupy all three 2, 4, and 6 positions, and n is 1 to 4; and (B) adding to said suspension about 1.0 to about 1.1 equivalents of bromine for each bromine atom to be substituted onto the aromatic ring of said substituted aniline and no acid is present during said reaction.

2. A method according to claim 1 wherein R is selected from the group consisting of trifluoromethoxy and trifluoromethyl.

3. A method according to claim 2 wherein R is trifluoromethoxy.

4. A method according to claim 1 wherein n is 1 and R is in the para position.

5. A method according to claim 1 wherein said reaction is performed at a temperature of about room temperature to about 60° C.

6. A method according to claim 5 wherein said reaction is performed at a temperature of about 40 to about 50° C.

7. A method according to claim 1 including the additional last steps of (1) separating said brominated substituted aniline by filtration;

(2) adding an oxidizing agent to the filtrate to oxidize hydrogen bromide therein to bromine; and (3) recycling said bromine to step (B).

8. A method according to claim 7 wherein said oxidizing agent is chlorine gas.

9. A method according to claim 4 wherein said brominating agent is liquid bromine.

10. A method according to claim 7 wherein about 1 to about 1.2 equivalents of said oxidizing agent are used.

11. A method according to claim 1 wherein about 2 to about 3 pbw of water are present per pbw of said substituted aniline.

12. A method according to claim 1 wherein a single bromine atom is substituted onto the aromatic ring of said substituted aniline.

13. A method according to claim 1 wherein two bromine atoms are substituted onto the aromatic ring of said substituted aniline.

14. A method of making 4-trifluoromethoxy-2,6-dibromoaniline comprising (A) forming a suspension in water of a 4-amino-trifluoromethoxybenzene in about 2 to about 3 pbw water;

(B) heating said suspension to about room temperature to about 60° C.; and (C) adding to said suspension about 2.0 to about 2.2 equivalents of bromine, where no acid is present in said suspension.

15. A method according to claim 14 wherein said reaction is performed at about 40 to about 50° C.

16. A method according to claim 14 including the additional last steps of (1) separating said brominated substituted aniline by filtration;

(2) adding an oxidizing agent to the filtrate to oxidize hydrogen bromide therein to bromine; and (3) recycling said bromine to step (C).

17. A method according to claim 16 wherein said oxidizing agent is chlorine gas.

18. A method according to claim 16 wherein the amount of said oxidizing agent is about 1 to about 1.2 equivalents.

19. A method of making 4-trifluoromethoxy-2,6-dibromoaniline comprising (A) forming a suspension of a 4-amino-trifluoromethoxybenzene in about 2 to about 3 pbw water;

(B) heating said suspension to about 40 to about 50° C.;

(C) adding to said suspension about 2.0 to about 2.2 equivalents of bromine, whereby said bromine reacts with said 4-amino-trifluoromethoxybenzene to form said 4-trifluoromethoxy-2,6-dibromoaniline and hydrogen bromide, where no acid is present during said reaction;

(D) separating said 4-trifluoromethoxy-2,6-dibromoaniline from said suspension by filtration;

(E) adding about 1 to about 1.2 equivalents of chlorine gas to the filtrate from step (D) to oxidize hydrogen bromide therein to bromine; and (F) recycling said bromine from step (E) to step (C).

20. A method according to claim 19 wherein said 4-trifluoromethoxy-2,6-dibromoaniline product is collected and washed with water.

* * * * *